(12) United States Patent
Buchanan

(10) Patent No.: US 6,731,968 B2
(45) Date of Patent: May 4, 2004

(54) MAGNETICALLY SHIELDED ROOM WITH INTERNAL ACTIVE MAGNETIC FIELD CANCELLATION, AND ITS USE

(75) Inventor: D. Scott Buchanan, Rancho Santa Fe, CA (US)

(73) Assignee: 4-D Neuroimaging, San Diego, CA (US)

( * ) Notice: Subject to any disclaimer, the term of this patent is extended or adjusted under 35 U.S.C. 154(b) by 22 days.

(21) Appl. No.: 10/189,092

(22) Filed: Jul. 3, 2002

(65) Prior Publication Data

US 2004/0006267 A1 Jan. 8, 2004

(51) Int. Cl.[7] .................................................. A61B 5/05
(52) U.S. Cl. .......................... 600/409; 324/260; 52/267
(58) Field of Search .............................. 600/407, 409; 324/260, 207.21; 52/267, 271

(56) References Cited

U.S. PATENT DOCUMENTS

| | | | |
|---|---|---|---|
| 5,081,071 A | | 1/1992 | Hirschkoff |
| 5,335,464 A | | 8/1994 | Vanesky et al. |
| 5,471,985 A | | 12/1995 | Warden |
| 5,494,033 A | | 2/1996 | Buchanan et al. |
| 5,603,196 A | * | 2/1997 | Sohlstrom ................... 52/796.1 |
| 6,208,884 B1 | * | 3/2001 | Kumar et al. ................ 600/409 |
| 6,282,848 B1 | * | 9/2001 | Schlapfer .................... 52/79.1 |

OTHER PUBLICATIONS ter Brake H, Wieringa H, Rogalla H, Improvement of the performance of a mu–metal magnetically shielded room by means of active compen–sation. Measurement Science & Technology, vol. 2, pp 595–601 (1991).

Skakala M, Zrubec V, Manka J, Active compensation for ambient mag–netic noise in the unshielded environment. Measurement Science & Technology, vol. 4, pp 468–472 (1993).

ter Brake H, Huonker R, Rogalla H, New results in active noise com–pensation for magnetically shielded rooms. Measurement Science & Technology, vol. 4, pp 1370–1375 (1993).

Aarnink W, van den Bosch P, Roelofs T, Verbeisen M, Holland H, ter Brake H, Rogalla H, Active noise compensation for multichannel Mag–netocardiography in an unshielded environment, IEEE Transactions on Applied Superconductivity, vol. 5(2), pp 2470–2473 (1995).

(List continued on next page.)

*Primary Examiner*—Eleni Mantis Mercader
(74) *Attorney, Agent, or Firm*—Eugene C Hirsckoff

(57) ABSTRACT

An apparatus includes an enclosure having a wall defining an interior of the enclosure and having a layer of a magnetically permeable material disposed such that there is no layer of an electrically conductive material located closer to the interior of the enclosure than the layer of the magnetically permeable material. A background-field magnetometer and an electrical coil structure are positioned within the enclosure. The electrical coil structure is driven by a controllable electrical current source. A background-field-reducing feedback controller has a controller input responsive to a background-field magnetometer output signal, and a controller output in communication with the current source command signal input. A signal magnetometer, such as a biomagnetometer, within the enclosure detects a magnetic field produced by a source within the enclosure. The electrical coil structure operating responsive to the feedback controller reduces the background magnetic field within the enclosure, so that the signal magnetometer may operate in an environment having less interference.

20 Claims, 3 Drawing Sheets

OTHER PUBLICATIONS

Urankar L, Oppelt R, Design criterions for active shielding of inho–mogeneous magnetic fields for biomagnetic applications. IEEE Trans–actions on Biomedical Engineering, vol. 43(7), pp 697–707 (1996).

Baum E, Bork J, Systematic design of magnetic shields. Journal of Magnetism and Magnetic Materials, vol. 101, pp 69–74 (1991).

Kato K, Yamazaki K, Matsuba H, Sumi C, Sato S, Active magnetic shield for biomagnetic measurements. Biomag 2000: Proceedings of the 12th International Conference on Biomagnetism. Ed. J. Nenonen.
Helsinki University of Technology, Espoo, Finland. pp. 965–967 (2001).

Holmlund C, Keipi M, Meinander T, Penttinen A, Seppa H, Novel con–cepts in magnetic shielding. Biomag 2000: Proceedings of the 12th International Conference on Biomagnetism. Ed. J. Nenonen. Helsinki University of Technology, Espoo, Finland. pp 968–969 (2001).

Kuriki S, Hayashi A, Hirata Y, Hybrid technique for reduction of environmental magnetic field noise. Biomag 2000: Proceedings of the 12th International Conference on Biomagnetism. Ed. J. Nenonen. Helsinki University of Technology, Espoo, Finland. pp 957–960 (2001).

* cited by examiner

MAGNETICALLY SHIELDED ROOM WITH INTERNAL ACTIVE MAGNETIC FIELD CANCELLATION, AND ITS USE

BACKGROUND OF THE INVENTION

This invention relates to the measurement of magnetic fields and, more particularly, to reducing the background magnetic field in the region space in which the measurement is made.

Biomagnetometer systems have been developed which have the necessary sensitivity to detect and measure the tiny magnetic fields naturally produced by the human brain and other parts of the human neurological system. Such biomagnetometer systems are described, for example, in U.S. Pat. Nos. 5,494,033 and 5,471,985, whose disclosures are incorporated herein by reference. In biomagnetometry, those magnetic fields produced by the body are measured and studied to diagnose disorders of the body as well as to understand the functioning of the body.

The magnetic fields produced by the human body are on the order of 1/10,000,000 of the strength of the background magnetic fields produced by the earth and by the equipment and infrastructure present in all urban environments. A major challenge to those wishing to practice biomagnetometry is to measure the tiny biomagnetic fields produced by the human body in the presence of the much larger and everpresent background magnetic fields. The most common approach to the solution of this problem is to perform the biomagnetic measurement in a magnetically shielded room or enclosure ("MSR"). Such MSRs are typically made up of several layers of highly magnetically permeable materials which serve to shield from the interior of the MSR the magnetic fields produced by sources outside the MSR, as well as electrically conductive layers which shield the interior of the MSR from external electromagnetic fields. Examples of such MSRs are described in U.S. Pat. Nos. 5,081,071 and 5,335,464, whose disclosures are incorporated by reference.

Magnetically shielded rooms which provide sufficient shielding to enable practical biomagnetometry on humans must attenuate the magnetic fields produced by sources outside the MSR by at least a factor of 100 and must be effective for both dc magnetic fields and ac magnetic fields at frequencies from about 0.01 Hz to several kiloHertz. As a result of this requirement, suitable MSRs require a large amount of highly magnetically permeable shielding material. Suitable MSRs are both expensive and heavy. Typical MSRs now available weigh about 16,000 pounds and cost about $500,000.

The high cost and large weight of these MSRs have limited the practice of both clinical and research biomagnetometry to those institutions which can afford such a cost and can provide permanent space in a building capable of housing such a structure. This limitation has prompted efforts to develop alternative ways of providing magnetic and electromagnetic shielding for a biomagnetometer that are effective, are of lower cost, are lighter in weight, and are easier to house in typical clinical and research buildings.

One approach to the provision of an alternative shielding method has been active cancellation. In this technique, magnetic field detectors detect the background magnetic field and provide command signals to electrical coils that are driven to produce a magnetic cancellation field that is opposite to the background magnetic fields. This active cancellation reduces the ambient magnetic field in the vicinity of the biomagnetometer, so that greater sensitivity is obtained in the biomagnetic measurements. Another approach has been the use of spatial filtering in which certain weighted sums of the output signals are particularly sensitive to sources very close to the biomagnetometer and much less sensitive to interference signals originating far from the biomagnetometer. Although these techniques have been successful to a degree, they still have not achieved the desired results in terms of providing adequate sensitivity for effective biomagnetometry combined with a reduction in the cost and weight of the MSR. Accordingly, there remains a need for a better approach to improving biomagnetic measurement results, while at the same time reducing the cost and weight of the required shielding. The present invention fulfills this need, and further provides related advantages.

SUMMARY OF THE INVENTION

The present invention provides an apparatus and a method for performing magnetic field measurements with a high degree of sensitivity in a typical urban hospital environment. The effects of background magnetic fields are reduced, and the cost, weight, and complexity of the shielding of the MSR are reduced. The present approach is particularly useful when applied in human biomagnetic measurements, which require a relatively large MSR enclosure to accommodate the person being measured.

In accordance with the invention, an apparatus comprises an enclosure having a wall defining an interior of the enclosure. The enclosure is preferably the size of a small room, at least about 500 cubic feet in volume. The wall comprises a layer of a highly magnetically permeable material disposed such that there is no layer of an electrically conductive material located closer to the interior of the enclosure than the layer of the highly magnetically permeable material. A background-field magnetometer, preferably a vector magnetometer, within the enclosure measures a background magnetic field and has a background-field magnetometer output signal. An electrical coil structure within the interior of the enclosure has an electrical coil input and produces a magnetic output field tending to nullify the background magnetic field. A controllable electrical current source has a current source output in communication with the electrical coil input, and a current source command signal input. A background-field-reducing feedback controller has a controller input responsive to the background-field magnetometer output signal, and a controller output in communication with the current source command signal input.

Preferably, the electrical coil structure includes at least three electrical coils arranged such that the output magnetic fields of the respective electrical coils are noncollinear, and wherein the current source output includes a separate current source output connected with each of the respective electrical coils.

The wall of the enclosure preferably comprises a layer of highly magnetically permeable material and a structure for mechanical support of that layer. The wall may also include one or more layers of additional shielding material. One or more of such additional layers may be made from electrically conducting material. But all such additional layers are disposed exteriorly of the layer of highly magnetically permeable material. The layer of highly magnetically permeable material is desirably mu metal.

The apparatus typically further comprises a signal magnetometer, preferably a biomagnetometer, positioned to detect a magnetic field produced by a source within the enclosure. The signal magnetometer may include a superconducting quantum interference device for high sensitivity.

In an active feedback system that partially or totally cancels the background magnetic field, the background-field magnetometer and the cancellation coils that are driven responsive to the signal measured by the background-field magnetometer must both be inside the enclosure of the MSR or both be outside the enclosure of the MSR. Otherwise, phase delays caused by the walls of the MSR prevent effective cancellation of the background magnetic field. In the past, it has been the practice to place both the background-field magnetometer and the cancellation coils outside of the enclosure of the MSR because it was believed that if the cancellation coils were placed inside the enclosure, electromagnetic reflections from the electrically conductive walls of the MSR would produce phase delayed "image" fields that would interfere with the desired cancellation of the background magnetic field. Such an approach has had only limited success, however, because the background-field magnetometer is located far from the signal magnetometer and outside the attenuating effect of the walls of the MSR; this has limited its usefulness to canceling highly uniform background fields.

The present approach places highly magnetically permeable material at the side of the wall of the MSR and requires that there is no sheet of electrically conductive material closer to the interior of the enclosure than is the sheet of the highly magnetically permeable material. It further places the background-field magnetometer and cancellation coils inside the MSR. Owing to the response characteristics of the highly magnetically permeable material comprising the inner surface of the enclosure to the magnetic fields produced by the cancellation coils, any phase delayed "image" fields are reduced so that effective cancellation of the background-field can be performed. The modified wall structure having the innermost layer of the highly magnetically permeable material and the positioning of the background-field magnetometer and the electrical coil structure within the enclosure cooperate to provide the benefits of the present approach. The background-field magnetometer and the electrical coil structure are positioned within the enclosure, thereby benefiting from the field-attenuating effects of the MSR wall, and are close to the signal magnetometer so that the cancellation field is representative of that found at the signal magnetometer.

Another benefit of the present approach is that the improved active magnetic-field cancellation allows the amount of the highly magnetically permeable material to be reduced. In current MSRs, there are typically 2–3 layers of the highly magnetically permeable material provided to achieve the necessary reduction of the internal magnetic field. With the improved magnetic-field cancellation of the present approach, typically only a single layer of the highly magnetically permeable material is required. The cost and weight of the MSR are thereby substantially reduced, both because large sheets of the highly magnetically permeable material are expensive and also because the supporting structure may be significantly reduced.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
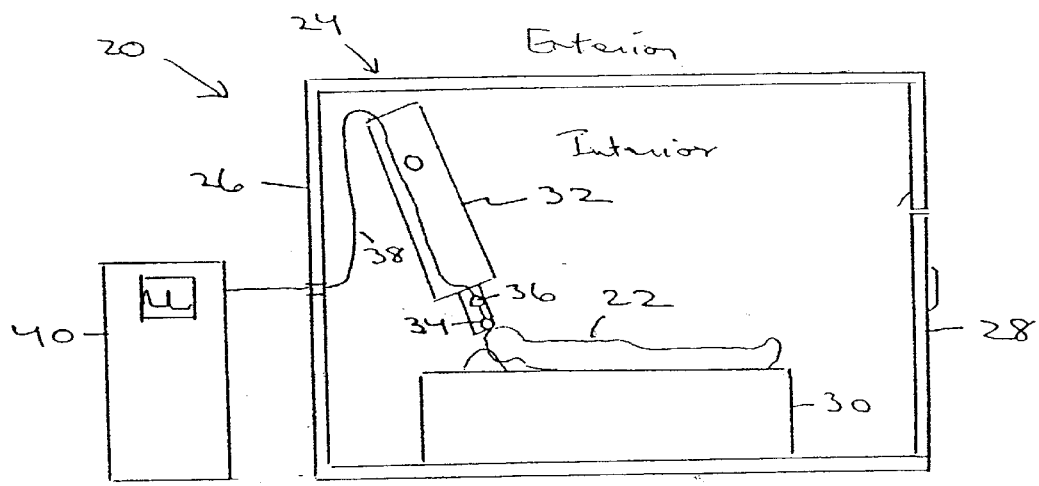
FIG. 1 is a schematic cross sectional view of a magnetically shielded room for biomagnetometry.

FIG. 1 depicts the general features of a magnetic measurement system 20 of the type used for performing biomagnetic measurements of a human being 22. An enclosure 24, which serves as a magnetically shielded room (MSR), has a wall 26, which includes a door 28. (As used herein, "walls" collectively includes the side walls, the top wall or ceiling, and the bottom wall or floor, as well as the door 28 through the side walls.) The enclosure 24 is sufficiently large to contain in its interior the human being 22, shown here reclining on a bed 30. The enclosure 24 is typically at least 500 cubic feet in volume, although in some cases it is significantly larger. A signal magnetometer 32, in this case a biomagnetometer, is positioned closely adjacent to the human being 22. The signal magnetometer 32 includes a magnetic field sensor 34, which provides its signal to a detector 36. The magnetic field sensor 34 is a sensitive pickup coil and the detector 36 is a superconducting quantum interference device for the biomagnetometer type of signal magnetometer 32. An output signal 38 of the detector 32 is conducted through a feedthrough to signal electronics 40, which is located exterior to the enclosure 24.

Figure 2:
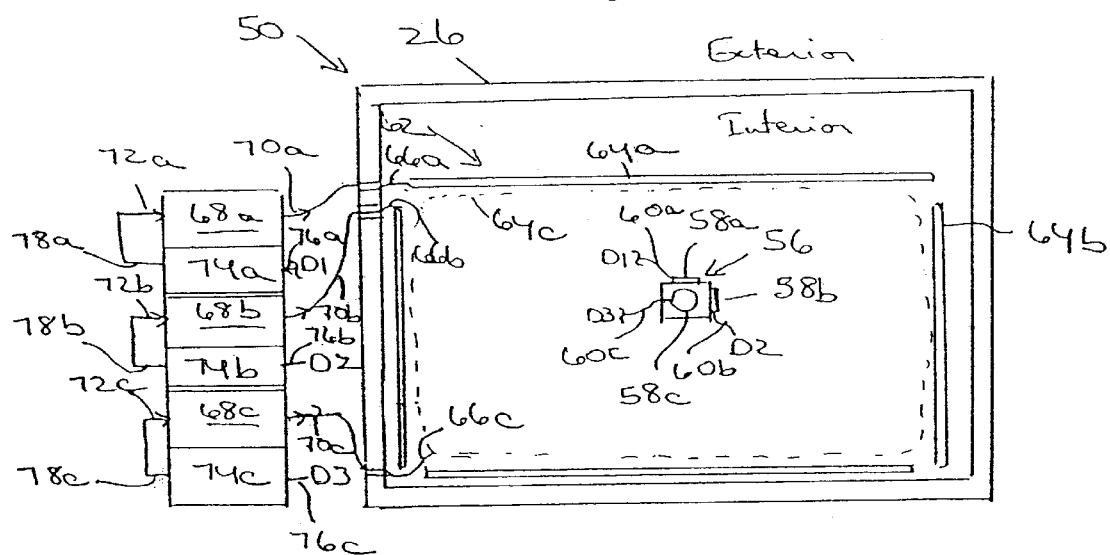
FIG. 2 is a schematic view of the apparatus of the invention.

An apparatus 50 for reducing the magnetic field and the electromagnetic field within a region of space is illustrated in FIG. 2. This apparatus 50 uses many of the same components illustrated in FIG. 1 and which are present in practice in the apparatus 50. The human being 22, bed 30, signal magnetometer 32, and signal electronics 40 have been omitted from FIG. 2 to avoid clutter and confusion with the elements that are illustrated in FIG. 2. Elements common to FIG. 1 are given the same reference numerals in FIG. 2, and the prior description is incorporated herein.

Figure 3:
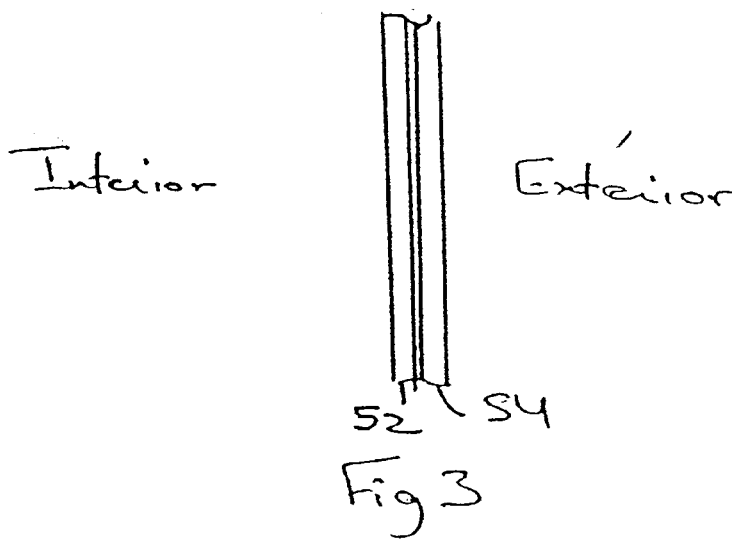
FIG. 3 is a cross-sectional view of the wall structure of the enclosure within the scope of the invention.

The apparatus 50 includes the enclosure 24 having the wall 26 defining an interior and an exterior of the enclosure 24. As seen in FIG. 3, the wall 26 comprises a layer 52 of a highly magnetically permeable material disposed such that there is no layer of an electrically conductive material located closer to the interior of the enclosure 24 than the layer 52 of the highly magnetically permeable material. In a preferred construction, the wall 26 further comprises a layer 54 to provide mechanical support which is not electrically conducting. In a second construction, layer 54 comprises an electrically conductive material, but the layer 52 of the highly magnetically permeable material is located closer to the interior of the enclosure 24 than is the layer 54 of the electrically conductive material.

Figure 4:
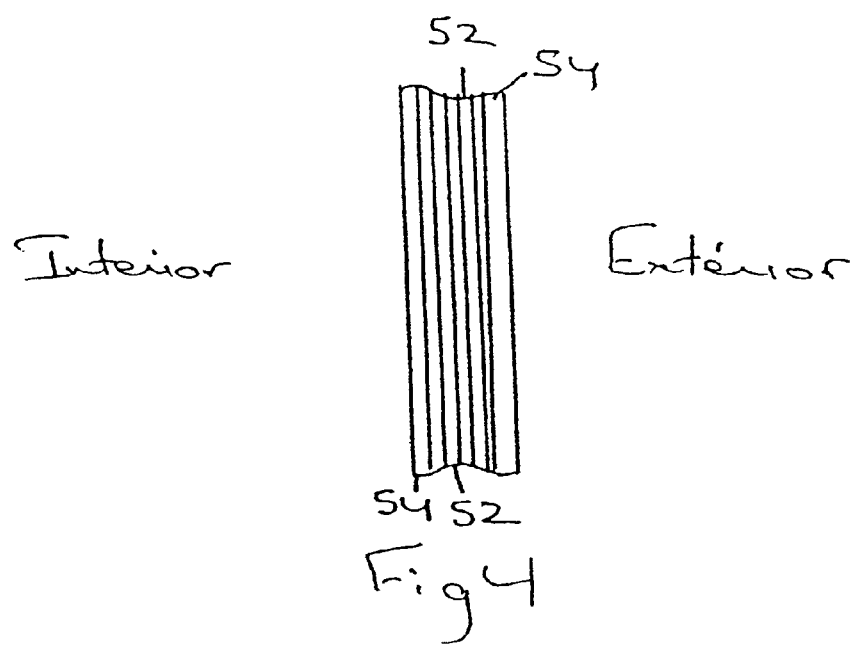
FIG. 4 is a cross-sectional view of an alternative wall structure not within the scope of the invention.

These constructions of the wall 26 may be contrasted with an alternative wall construction for a magnetically shielded room, as shown in FIG. 4. In this construction, one or more layers (in this case two) 52 of highly magnetically permeable material are sandwiched between two layers 54 of electrically conductive material. This approach is not amendable to the active cancellation technique discussed subsequently, because the layer 54 rather than the layer 52 is closest to the interior of the enclosure 24.

The layer 52 of the highly magnetically permeable material is made of a material having an initial magnetic permeability of more than about 4000. The magnetic permeability must be more than about 4000 to provide sufficient shielding against the external magnetic fields. The layer 52 is preferably made of mu metal, which has a composition of 77% nickel, 14% iron, 5% copper, and 4% molybdenum and has an initial magnetic permeability of about 60,000. In a typical embodiment, the layer 52 has a thickness of about 2 mm.

A background-field magnetometer 56 is positioned within the enclosure 24. The background-field magnetometer 56 measures the ambient magnetic field within the enclosure 24, apart from the magnetic field produced by the human being 22 or other magnetic-field source within the enclosure 24. In the preferred case, the background-field magnetometer 56 is a vector magnetometer which can measure the components of the background magnetic field vector. The illustrated background-field magnetometer 56 has three approximately orthogonal magnetic field sensors 58a, 58b, and 58c, each with its respective background-field magnetometer output signal 60a, 60b, and 60c. The apparatus 50 further includes an electrical coil structure 62 within the interior of the enclosure 24. The electrical coil structure 62 produces a magnetic output field responsive to an electrical coil input. The electrical coil structure 62 comprises at least one electrical coil. Some of the electrical coils making up the electrical coil structure 62 may be constructed to produce an approximately uniform magnetic field in the region of the signal magnetometer 32. Some of the electrical coils making up the electrical coil structure 62 may be constructed to produce a magnetic field gradient in the region of the signal magnetometer 32. The selection of the constructions of the electrical coils making up the electrical coil structure 62 is made to provide the most complete cancellation of a particular background magnetic field.

Preferably, the electrical coil structure 62 includes at least three electrical coils arranged such that output magnetic field vectors of the respective electrical coils are noncollinear. Each of the electrical coils has a separate electrical coil input. In the most preferred embodiment which is illustrated, the electrical coil structure 62 includes three electrical coils 64a, 64b, and 64c. The output magnetic field vectors of the respective electrical coils 64a, 64b, and 64c are orthogonal. Each of the electrical coils 64a, 64b, and 64c has a respective electrical coil input 66a, 66b, and 66c.

The apparatus 50 includes a controllable electrical current source having a current source output in electrical communication with the respective electrical coil input, and a current source command signal input. In the illustrated embodiment, there are three independent electrical current sources 68a, 68b, and 68c. Each electrical current source 68a, 68b, and 68c has a respective current source output 70a, 70b, and 70c in electrical communication with the respective electrical coil input 66a, 66b, and 66c. Each electrical current source 68a, 68b, and 68c has a respective current source command signal input 72a, 72b, and 72c.

The apparatus 50 further includes a background-field-reducing feedback controller having a controller input responsive to the background-field magnetometer output signal, and a controller output in electrical communication with the current source command signal input. In the illustrated embodiment, there are three background-field reducing feedback controllers 74a, 74b, and 74c having respective controller inputs 76a, 76b, and 76c responsive to the respective background-field magnetometer output signals 60a, 60b, and 60c. Each background-field reducing feedback controller 74a, 74b, and 74c has a respective controller output 78a, 78b, and 78c in electrical communication with the respective current source command signal input 72a, 72b, and 72c.

Figure 5:
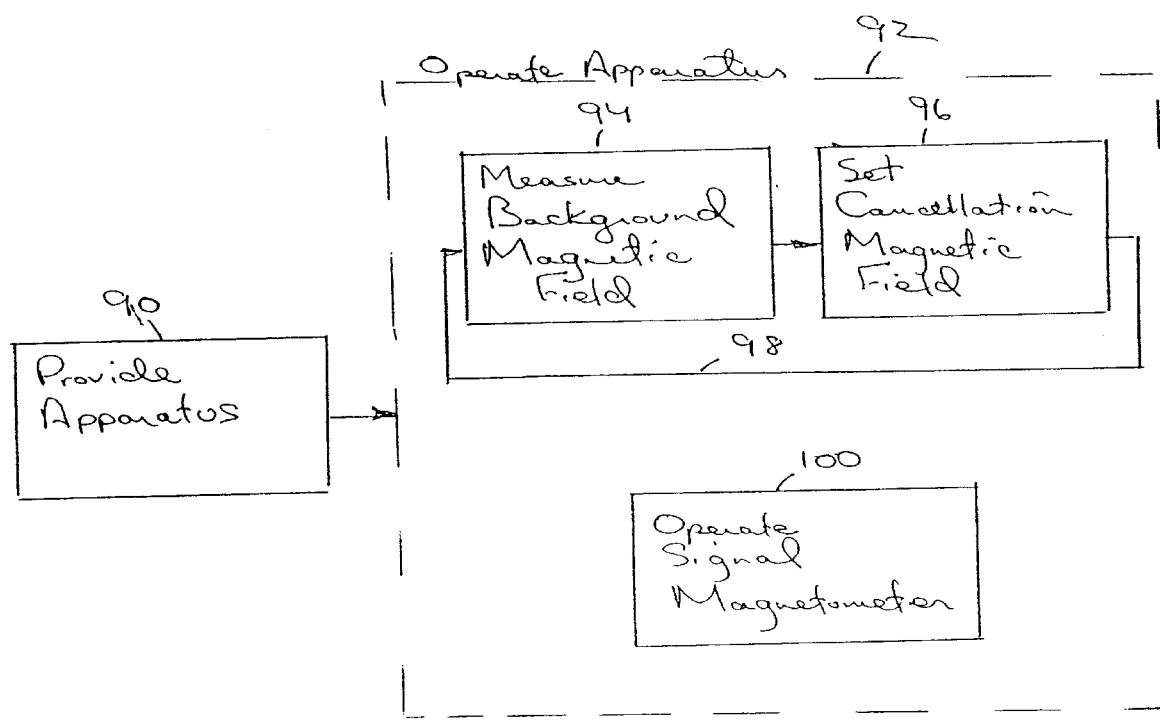
FIG. 5 is a block diagram of an approach for practicing the invention.

FIG. 5 illustrates a preferred approach for practicing the invention. The apparatus 50, including the magnetic measurement system 20, is provided, numeral 90. The apparatus 50 is operated, numeral 92. During this operation, two subsystems are operated simultaneously. The background magnetic field is measured, numeral 94. In this measurement 94, the magnetic field sensor coils 58a–c detect the orthogonal components of the background magnetic field within the interior of the enclosure 24 at a location at or near the magnetic field sensor 34 of the signal magnetometer 32. The cancellation magnetic field is set, numeral 96, by a feedback procedure. The respective background-field magnetic output signals 60a–60c are provided as respective controller inputs 76a–76c to the respective background-field reducing feedback controllers 74a–74c. The background-field reducing feedback controllers 74a–74c determine the three orthogonal cancellation magnetic fields and currents to the electrical coils 64a–64c required to reduce, preferably to null, the respective orthogonal components of the background magnetic field. These required currents are controller outputs 78a–78c provided as the respective current source command signal inputs 72a–72c to the respective electrical current sources 68a–68c. The currents produced are output as current source outputs 70a–70c to the respective electrical coil inputs 66a–66c and thence to the respective electrical coils 64a–64c. The steps 94 and 96 are continuously repeated, as indicated by line 98, to maintain the orthogonal components of the background magnetic field as measured by the background-field magnetometer 56 each as close to zero as possible.

Simultaneously with steps 94, 96, and 98, the signal magnetometer 32 is operated, numeral 100. In the preferred application, the signal magnetometer is the biomagnetometer measuring magnetic field signals produced by the human being 22. The combination of the structure of the wall 26 of the enclosure 24 and the active magnetic field cancellation discussed in relation to FIG. 2 produces a background magnetic field in the neighborhood of the magnetic field sensor 34 of the signal magnetometer 32 close to zero, so that the magnetic field sensor 34 may operate with maximum sensitivity.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An apparatus comprising:
   an enclosure having a wall defining an interior of the enclosure, the wall comprising a layer of a magnetically permeable material disposed such that there is no layer of an electrically conductive material located closer to the interior of the enclosure than the layer of the magnetically permeable material;
   a background-field magnetometer within the enclosure and having a background-field magnetometer output signal;
   an electrical coil structure within the interior of the enclosure and producing a magnetic output field responsive to an electrical coil input;
   a controllable electrical current source having
      a current source output in communication with the electrical coil input, and
      a current source command signal input; and a background-field-reducing feedback controller having a controller input responsive to the background-field magnetometer output signal, and a controller output in communication with the current source command signal input.

2. The apparatus of claim 1, wherein the electrical coil structure includes at least three electrical coils each producing a magnetic field output responsive to a respective electrical coil input and arranged such that output magnetic field vectors of the respective electrical coils are noncollinear, and wherein the current source output includes a separate current source output connected with the electrical coil input of each of the respective electrical coils.

3. The apparatus of claim 1, wherein the electrical coil structure includes at least eight electrical coils arranged such that each electrical coil produces a magnetic output field gradient responsive to a respective electrical coil input and arranged such that no two magnetic output field gradients produced are redundant with each other, and wherein the current source output includes a separate current source output connected with the electrical coil input of each of the respective electrical coils.

4. The apparatus of claim 1, where in the electrical coil structure includes at least one electrical coil which produces a magnetic output field responsive to a respective electrical coil input and at least one electrical coil which produces a magnetic output field gradient responsive to a respective electrical coil input, and wherein the current source output includes a separate current source output connected with the electrical coil input of each of the respective electrical coils.

5. The apparatus of claim 1, wherein the background-field magnetometer is a vector magnetometer.

6. The apparatus of claim 1, wherein the background-field magnetometer includes a magnetic gradiometer.

7. The apparatus of claim 6, wherein the signal magnetometer comprises a superconducting quantum interference device.

8. The apparatus of claim 6, wherein the signal magnetometer is a biomagnetometer.

9. The apparatus of claim 1, wherein the wall comprises the layer of magnetically permeable material, and a layer of an electrically conductive material disposed exteriorly of the layer of magnetically permeable material.

10. The apparatus of claim 1, wherein the layer of magnetically permeable material comprises mu metal.

11. The apparatus of claim 1, wherein the layer of magnetically permeable material comprises material with an initial magnetic permeability greater than 4000.

12. The apparatus of claim 1, wherein the apparatus further comprises:

a signal magnetometer positioned to detect a magnetic field produced by a source within the enclosure.

13. The apparatus of claim 1, wherein the interior of the enclosure has a volume of at least about 500 cubic feet.

14. The apparatus of claim 1, wherein the layer of magnetically permeable material comprises material with an initial magnetic permeability greater than 4000.

15. An apparatus comprising:

an enclosure having a wall defining an interior of the enclosure, the wall comprising a layer of a magnetically permeable material, and an innermost layer of an electrically conductive material disposed exteriorly of the layer of the magnetically permeable material;

a background-field magnetometer within the enclosure and having a background-field magnetometer output signal;

an electrical coil structure within the interior of the enclosure and having an electrical coil input;

a controllable electrical current source having a current source output in communication with the electrical coil input, and a current source command signal input;

a background-field-reducing feedback controller having a controller input responsive to the background-field magnetometer output signal, and a controller output in communication with the current source command signal input; and a signal magnetometer positioned to detect a magnetic field produced by a source within the enclosure.

16. The apparatus of claim 15, wherein the electrical coil structure includes at least three electrical coils each producing a magnetic field output responsive to a respective electrical coil input and arranged such that output magnetic field vectors of the respective electrical coils are noncollinear, and wherein the current source output includes a separate current source output connected with the electrical coil input of each of the respective electrical coils.

17. The apparatus of claim 15, wherein the electrical coil structure includes at least eight electrical coils arranged such that each electrical coil produces a magnetic output field gradient responsive to a respective electrical coil input and arranged such that no two magnetic output field gradients produced are redundant with each other, and wherein the current source output includes a separate current source output connected with the electrical coil input of each of the respective electrical coils.

18. The apparatus of claim 15, where in the electrical coil structure includes at least one electrical coil which produces a magnetic output field responsive to a respective electrical coil input and at least one electrical coil which produces a magnetic output field gradient responsive to a respective electrical coil input, and wherein the current source output includes a separate current source output connected with the electrical coil input of each of the respective electrical coils.

19. The apparatus of claim 15, wherein the layer of magnetically permeable material comprises mu metal.

20. The apparatus of claim 15, wherein the signal magnetometer is a biomagnetometer.

* * * * *